United States Patent [19]

Gluckman et al.

[11] Patent Number: 5,276,014
[45] Date of Patent: Jan. 4, 1994

[54] TREATMENT OF HUMAN LACTATION FAILURE

[75] Inventors: Peter Gluckman; Stella R. Milsom, both of Auckland, New Zealand

[73] Assignee: Kabi Pharmacia AB, Upsala, Sweden

[21] Appl. No.: 765,171

[22] Filed: Sep. 26, 1991

[51] Int. Cl.$^5$ .................... A61K 37/02; A61K 37/36; A61K 37/43; A61K 31/475

[52] U.S. Cl. ........................ 514/12; 514/21; 530/303; 530/399

[58] Field of Search ............ 514/12, 21; 530/399, 530/303, 324, 350

[56] References Cited

U.S. PATENT DOCUMENTS

| | | | |
|---|---|---|---|
| 4,783,524 | 11/1988 | Larsen et al. | 530/324 |
| 5,061,690 | 10/1991 | Kann et al. | 514/12 |

FOREIGN PATENT DOCUMENTS

| | | |
|---|---|---|
| 193917 | 9/1986 | European Pat. Off. |
| 212531 | 3/1987 | European Pat. Off. |
| 216742 | 4/1987 | European Pat. Off. |
| 237514 | 9/1987 | European Pat. Off. |
| 314866 | 5/1989 | European Pat. Off. |
| 319049 | 6/1989 | European Pat. Off. |
| WO9002182 | 3/1990 | PCT Int'l Appl. |

OTHER PUBLICATIONS

Abribat et al. Domestic Animal Endocrinology vol. 7(1); 93–102, 1990.

Primary Examiner—Michael G. Wityshyn
Assistant Examiner—Choon Koh
Attorney, Agent, or Firm—Pollock, Vande Sande & Priddy

[57] ABSTRACT

The invention relates to the use of hGH, hGRF, hIGF-1, hIGF-2 or analogs of these or a mixture of two or more of these, alone or in conjunction with lactational enhancers for the treatment of human lactation failure. It also relates to the use of hGH, hGRF, hIGF-1, hIGF-2 or analogs of these or a mixture of two or more of these, alone or in conjunction with lactational enhancers for the manufacturing of a medicament for the treatment of human lactation failure, also a profphlactic treatment. Preferably human growth hormone is used. The invention also relates to a method for the treatment of human lactation failure as well as compositions and methods for their manufacturing.

9 Claims, No Drawings

TREATMENT OF HUMAN LACTATION FAILURE

FIELD OF INVENTION

This invention relates to the use of human growth hormone (hGH), human growth hormone releasing factor (hGRF), human insulin-like growth factor (hIGF-1 and hIGF-2) or analogs of these or a mixture of two or more, alone or in conjunction with lactational enhancers for the treatment of human lactation failure.

BACKGROUND

Endogenous Growth Hormone (GH) plays an important role in the establishment (mammogenesis) and maintenance (lactogenesis) of ruminant lactation (Cowie et al. In "Lactation", 123-140 Ed. I. R. Falconer 1971, Vines et al. J. Dairy Sci 60: 1949-1957, 1977).

It is known that serum levels of endogenous GH are greater in high yielding than low yielding cows (Hart et al, Endocr. 77:333-345, 1978) and in animal studies it has been shown that a synergistic effect of GH together with other lactogenic hormones is obtained in the development of the mammary gland (Tucker J. Dairy Sci 64: 6: 1403-1421, 1981). The site of action of GH is less clear, as limited animal studies have failed to show binding of labelled GH to mammary tissue, suggesting GH receptors are not present in the gland in significant concentrations. Recent advances in understanding the mode of action of GH via insulin-like growth factors and the identification of various growth factors in mammary secretions suggest that GH may mediate its effect on the mammary gland via insulin-like growth factors (IGFs). (Phillips et al NEJM 302: 371-378, 1980, Baxter et al J. Clin Endocrinol Metab 58: 955-959, 1984, Corps et al J. Clin. Endocrinol Metab 67; 25-29, 1988) although there is contradictory data (Davis et al. J. Endocrinol 123,33, 1989).

It is not known if these growth factors are produced locally, or transferred from the maternal circulation and what influence maternal and milk levels of these peptides have an initial lactation, maintenance of lactation and neonatal growth.

For many years it has also been known that exogenous GH will significantly increase the milk yield in cattle (Machlin et al. J. Dairy Sci 56: 575-580, 1973) although close arterial infusions of GH into the mammary gland of ruminants does not increase milk yield, suggesting an indirect effect (Mc Dowell et al. Aust J Biol Sciences 40, 181-189. 1987).

The mechanism of GH-potentiated boosting of milk yields remains unknown, although several lines of research suggest that the most likely mode of action is via insulin-like growth factors acting either directly or indirectly. IGFs have now been found in the mammary secretions of various animals and more recently in milk samples from lactating mothers up to 6 months post partum.

While considerable knowledge has thus been obtained recently regarding animal lactation, this knowledge has to date not been extended to the human.

However in the non-ruminant, the role of growth hormone in lactation is much less defined and is likely to be very minor. GH may play a part in mammogenesis, but in lactogenesis the most important controlling hormone seems to be prolactin (Shiu RPC et al. Annu. Rev. Physiol 42:83-96, 1980). Prolactin receptors are present in mammary tissue (Shiu et al. Biochem J 140:301, 1974), indicating a direct effect of prolactin on the breast, and prolactin mediated events such as the incorporation of tritiated leucine into casein are blocked by antibodies to the prolactin receptor. (Shiu et al. Science 192: 259, 1976). Prolactin levels rise during suckling and basal levels are also elevated during the initial weeks of lactation (Noel GL et al. J Clin Endocrinol Metab 38:413-423, 1974). If levels are lowered e.g. by ergot drugs, lactation ceases.

Conversely, neuropharmacologic agents which block inhibition of prolactin release such as Reserpine (11,17-dimethoxy-18-((3,4,5-trimethoxybenzoyl)oxy)yohimban-16-carboxylic acid methyl ester) and Metoclopromide (4-amino-5-chloro-N-((2-diethylamino)ethyl)-2-methoxybenzamide), increase serum prolactin levels with a positive effect on lactation volumes. (Guzman et al. Acta Obstet Gynaecol Scand 58:53-55, 1979). These effects of pharmacologic intervention on prolactin levels and subsequent changes in lactation volumes are mirrored in several pathological conditions seen clinically. In Sheehans syndrome (pituitary failure following childbirth) prolactin levels are considerable diminished, with subsequent failure of affected mothers to establish lactation. Conversely, in situations of prolactin excess, e.g. prolactin-secreting tumours, the clinical presentation is often inappropriate lactation in both sexes. (Kleinberg et al. N. Eng J Medicine, 296:589-600, 1977). In contrast growth hormone levels are low throughout lactation and do not rise with suckling.(See Noel GL et al above). It is also known that ateliotic (GH-deficient) female dwarves lactate normally (See Rimoin DL et al J. Clin Endo Metab. 28,1183-88. 1986). Therefore the weight of evidence supports prolactin as the dominant hormone in human lactogenesis and any role for growth hormone in this situation appears minor.

Failure of normal lactation is a well established entity in man and causes considerable emotional distress to the affected mother. Current treatment options are relatively limited. Available drugs such as Reserpine and Metoclopromide are often used because their pharmacologic actions include stimulating release through dopamine pathways. However they can cause disadvantageous side effects, e.g. sedation and/or hypotension in a significant proportion of mothers and because they are probably, like sulpiride (another procainamide analogue), excreted in breast milk, could have potentially toxic effects for the infant. (See Aono T et al J. Clin. Endocrinol. Metab. 47:675-680, 1978).

Alternative treatment approaches are clearly required. An obvious approach to this problem would be to directly increase maternal prolactin levels by supplementation. Unfortunately recombinant prolactin is not available for a large scale trial of this treatment and pituitary derived prolactin has now been found to be unsafe, following cases of Jacob-Creuzfield disease in children treated with pituitary derived hormones. Recombinant human growth hormone, however, is readily available.

Lactation failure in humans is a common clinical event with serious emotional sequelae. It has been considered to be a significant problem in 5 to 10% of all lactations. In many instances this leads to premature initiation of supplements or total weaning. This is considered to be an inferior child rearing practice and may be harmful to certain infants with an increased risk of gastritis etc. Many affected women are severely emotionally distressed by their perceived inadequacy, thus effecting the parent-child bond. Failure to thrive in infants is not uncommon if the mother refuses to supplement.

There has therefore been a long need for a medicament, which can promote human lactation e.g. when there is a lactation failure after the birth of the child. This is a human problem. For animals like cow and goat, there has only been a need for an increase of the milk production above a normal level.

In EP 317 387 it is suggested that the production of milk and the weight of the new born child as well as the post partum weight gain in animals and in humans will increase, when an effective amount of hGRF is given to the mother before child birth. The animal is treated for a short time (10-20 days). No experiments have been carried out on humans and in the examples only sheep have been used and any effect was probably indirect through stimulation of mammogenesis late in gestation, given the short half life of hGRF.

There is no substantive or direct evidence that in man growth hormone has a significant role in lactogenesis (Rimoin DL et al. J. Clin. Endocrinol Metab. 28:1183–1188, 1968).

There has been no reason to suppose that hGH would be useful in human lactation failure and no one has yet examined the use of hGH for lactation failure in the newly delivered human mother.

DESCRIPTION OF THE INVENTION

The present invention relates to the use of hGH, hGRF, hIGF-1, hIGF-2 or analogs of these or a mixture of two or more of these alone or in conjunction with lactational enhancers for the treatment of human lactation failure.

It also relates to the use of hGH, hGRF, hIGF-1, hIGF-2 or analogs of these or a mixture of two or more of these, alone or in conjunction with lactational enhancers for the manufacturing of a medicament in the treatment of human lactation failure.

The invention also relates to a prophylactic treatment of expectant mothers who are at special risk for lactation failure.

Preferably human growth hormone is used in a dose of 0.05-1, more preferably 0.1-0.4 and especially 0.1-0.2 IU/kg/day.

The lactational enhancers could be chosen among 11,17-dimethoxy-18-((3,4,5-trimethoxybenzoyl)oxy)yohimban-16-carboxylic acid methyl ester or 4-amino-5-chloro-N-((2-diethylamino)ethyl)-2-methoxybenzamide.

The invention also relates to a method for the treatment of human lactation failure, characterized in that hGH, hGRF, hIGF-1, hIGF-2 or analogs of these or a mixture of two or more of these, alone or in conjunction with lactational enhancers, is administered to a woman. This administration could be subcutaneous, intramuscular, intravenous, nasal or dermal, preferably subcutaneous.

The invention also relates to a composition comprising hGH, hGRF, hIGF-1 or hIGF-2 or analogs of these or a mixture of two or more of these in conjunction with lactational enhancers, together with pharmaceutically acceptable carriers for the treatment of human lactation failure, as well as a method for the manufacturing of these compositions.

By lactation failure is here meant both when the woman has no or insufficient amount of milk or is at special risk for that.

By hGH is here meant both natural occuring human GH and recombinant hGH (rhGH). By analogs of hGH and hGRF are meant compounds having the same therapeutic effect as GH and GRF respectively in humans, and hIGF-analogs having the potential to mediate the actions of growth hormone in humans.

The lactation can be promoted in the following situations:

i) To normalize lactation volumes in women with lactational failure ii) To maintain/enhance lactation in mothers of premature babies who are being cared for in a neonatal unit iii) To enhance lactational performance in mothers with twins and triplets iv) To promote and prolong lactation in mothers of babies with risk of developing lactose intolerance or other milk allergies if formula milk was used v) To promote/prolong lactation in mothers where adverse hygiene conditions would make the use of formula undesirable vi) To enhance lactation in women where suckling frequency is diminished during part of the day, e.g. working mothers vii) To treat mothers prophylactically prior partus with a special risk for having an insufficient amount of milk production.

In the following study, supporting the invention we have found the following:

1. We have shown hGH treatment of normally lactating women to have no deleterious effect on milk quality or to leave hormone residues.
2. We have examined hGH treatment in normally lactating women and demonstrated a major increase in milk production.
3. Preliminary data obtained from treating women suffering from lactation failure with hGH shows this treatment is effective in enhancing lactation performance.

EXAMPLES

1. The objective of this study was to study the effect of hGH treatment on milk quality.

Four patients were studied immediately following weaning to ensure that short course growth hormone therapy had no adverse effect on milk biochemistry. The mothers were not suckling.

Day 1-2 were control days, rhGH was administered on days 3-6 (0,1 U/kg/day) and samples were taken also on day 7, 24 hours after the last rhGH injection.

Milk samples were obtained daily, and serum on day 1 (control) and in addition, before and one hour after rhGH injection.

| Results of the analysis of the milk: | | | |
|---|---|---|---|
| | Control Day | Day 6 | Paired t test |
| Total protein (g/L) | 17.9 ± 3.9 | 19.5 ± 3.3 | NS |
| Calcium (mmol/L) | 5.9 ± 0.26 | 4.4 ± 1.2 | NS |
| Sodium (mmol/L) | 38.1 ± 9.1 | 50.3 ± 14.2 | NS |
| Potassium (mmol/L) | 12.2 ± 0.1 | 10.8 ± 0.7 | NS |
| Albumin | 4.1 ± 0.3 | 4.3 ± 0.5 | NS |

-continued

| Results of the analysis of the milk: | | | |
|---|---|---|---|
| (g/L) | Control Day | Day 6 | Paired t test |

NS means not significant difference between mean levels of control day and day 6.

rhGH administration does thus not appear to cause any major changes in milk composition.

2. The objective of this study was to assess whether hGH treatment enhances milk production in normally lactating women.

Nineteen patients (27-37 years), normally lactating after delivery and who were breast feeding at 8-15 weeks were studied in a double blind trial. Three of these patients were excluded from analysis as the trial protocol was not adhered to. Eight of the patients were given placebo and 8 of the patients were given rhGH as Genotropin ®, in Kabipen, 0,1 U/kg/day, using the same regimen for one week at approximately 8 weeks post partum.

During day 1 and day 2 the patients had no treatment and during day 3-9 they were given rhGH or placebo at 9 a.m. Lactation performance was assessed on day 2 (control day) and day 9 (7th day of rhGH treatment) by a 24 hour testweigh period, V2 and V9 respectively. (mls)

The infant was weighed before and post each feed on standard accurate scales to an accuracy of 5 g. Once the infant was fed, the remainder of the milk was expressed by pump (and the volume measured to 1 ml and expressed as grams). The two amounts were added for each feed. The sum for the 24 hour period equals the total daily milk production.

Milk samples were also collected daily and serum samples on days 1, 4, 6 and 10 for analysis of GH, IGF-1 and milk quality parameters.

| | Results: | | | |
|---|---|---|---|---|
| | V2 | V9 | V9 − V2 | % change |
| Patient rhGh treatment | | | | |
| 1 | 947 | 1192 | 245 | +25.5 |
| 2 | 913 | 1124 | 211 | +23.5 |
| 3 | 1045 | 1239 | 194 | +18.5 |
| 4 | 712 | 843 | 131 | +18.4 |
| 5 | 780 | 922 | 142 | +18.0 |
| 6 | 611 | 708 | 97 | +16.0 |
| 7 | 616 | 704 | 88 | +14.3 |
| 8 | 1055 | 1202 | 147 | +13.9 |
| patient, placebo | | | | |
| 1p | 796 | 948 | 152 | +19.1 |
| 2p | 770 | 909 | 139 | +18.0 |
| 3p | 843 | 976 | 133 | +15.8 |
| 4p | 969 | 1093 | 124 | +13.0 |
| 5p | 773 | 846 | 73 | +9.4 |
| 6p | 1260 | 1358 | 98 | +7.8 |
| 7p | 678 | 719 | 41 | +6.0 |
| 8p | 749 | 782 | 33 | +4.0 |

The result was as follows when expressed as percentage increment in milk yield over baseline:

| | n | mean | standard deviation | standard error |
|---|---|---|---|---|
| rhGH | 8 | +18.5% | 4.12% | 1.45% |
| Placebo | 8 | +11.6% | 5.67% | 2.00% |

Thus rhGH stimulates lactation highly significantly in comparison with the placebo treated control group (Student t- test t=2.77 p<0.02) in normal lactating women. The placebo effect was a little higher than we would have anticipated. In addition to the expected effect of a nurse taking care of the mother and measuring the milk the use of breast pump to remove residual milk may act as a further stimulus to lactation.

No significant differences were seen in the concentration of fat, lactose, protein or electrolytes in breast milk after treatment in the two groups. Basal GH levels in milk were low in both groups (mean 0.45 ug/L in the placebo group, mean 0.61 ug/L in the GH group) and were not altered significantly by treatment in either group (mean 0.55 ug in the placebo group, mean 0.65 ug in the GH treated group) on day 10. There were no adverse clinical events during the study.

3. The objective of this study was to assess whether hGH treatment enhances milk production in women suffering from lactation failure.

Lactation failure is in this study based on the following observations:

a) baby dissatisfied and irritable after feeds
b) poor infant weight gain in relation to age/length
c) lack of breast engorgment/leaking if feed missed
d) supplemental feed following breast feed contents baby.

The selection criteria were mothers of term babies with perceived lactation failure and who were documented to secrete less than 500 ml/day and who were between 4 and 16 weeks in lactation.

In this study the women were given no injection during day 1 and then rhGH, 0.05, 0.1 and 0.2 IU/kg/day, respectively, at 9 a.m. from day 2 to 8 inclusive.

Up to now three groups of women have been treated. The results were as follows:

| Group | n | Amount, IU/kg. day | % increase in lactation (±SE) |
|---|---|---|---|
| A | 3 | 0.05 | −1.1 ± 5.6 |
| B | 4 | 0.1 | 19.8 ± 8.6 |
| C | 4 | 0.2 | 12.4 ± 3.1 |
| B + C | 8 | | 16.1 ± 4.52 |

A versus B: p=0.05.

A versus B+C combined: p<0.033 (t test tailed) and p<0.04 (Mann-Whitney)

This shows that treating women with lactation failure with growth hormone significantly effects milk production and shows dose dependency. Even this small number of patients treated shows statistically an effect.

SUMMARY

1(i). Growth hormone supplementation of the mother does not adversely affect milk quality. Milk of treated mothers was assayed for sodium, potassium, fat total protein and lactose content and there were no significant differences before and after treatment for any of these analytes.

1(ii). Growth hormone excretion into milk is not increased. The mean level of milk GH was 0.61±0.14 on the control day and 0.65±0.24 after 7 days of GH treatment (p=NS).

2. The result of our double-blind placebo controlled trial of growth hormone in normally lactating women strongly supports a major effect of GH on lactogenesis. Milk volumes (as assessed by 24-hour test weighs conducted according to WHO criteria) were increased by a mean of 18.5% in the treated group compared with 11.2% in control group (p<0.02).

3. Data from women with lactation failure treated with growth hormone show that lactation performance is enhanced. Three women have been treated with 0.1 IU/kg/day and the mean response was 19.8% increase, and for four women receiving 0.2 IU/kg,day there was a 12.4% increase in milk volume.

We claim:

1. A method of treating a human patient exhibiting no or an insufficient amount of milk production or at special risk for such by administering to said patient after birth an effective amount of human growth hormone, human insulin-like growth factor-1, human insulin-like growth factor-2 or analogs of these, or a mixture of two or more of these alone or in conjunction with lactational enhancers.

2. The method according to claim 1, wherein said administration is subcutaneous, intramuscular, intravenous, nasal, oral, or dermal.

3. The method according to claim 1, wherein human growth hormone is administered to the patient.

4. The method according to claim 3, wherein the dose of human growth hormone administered to the patient is 0.05-1 IU/kg/day.

5. The method according to claim 3, wherein the dose of human growth hormone administered to the patient is 0.1-0.4 IU/kg/day.

6. The method according to claim 3, wherein the dose of human growth hormone administered to the patient is 0.1-0.2 IU/kg/day.

7. The method according to claim 1, wherein the lactational enhancers are selected from the group consisting of 11,17-dimethoxy-18-((3,4,5-trimethoxybenzoyl)oxy)yohimban-16-carboxylic acid methyl ester and 4-amino-5-chloro-N((2-diethylamino)ethyl)-2-methoxybenzamide.

8. A composition of matter, comprising:
at least one compound selected from the group consisting of human growth hormone, human insulin-like growth factor-1, human insulin-like growth factor-2 or analogs of these and at least one lactational enhancer selected from the group consisting of 11,17-dimethoxy-18-((3,4,5-trimethoxybenzoyl)oxy)yohimban-16-carboxylic acid methyl ester and 4-amino-5-chloro-N((2-diethylamino)ethyl)-2-methoxybenzamide.

9. The composition of matter according to claim 8, wherein said composition of matter also includes a pharmaceutically acceptable carrier.

* * * * *